United States Patent [19]
Stephens et al.

[11] Patent Number: 5,209,736
[45] Date of Patent: May 11, 1993

[54] TROCAR METHOD AND APPARATUS

[75] Inventors: Randy R. Stephens, Fairfield; Dale R. Schulze, Lebanon; Gregory D. Bishop, Hamilton; Narinderjit Sambi, Maineville, all of Ohio; John M. Collins, Ipswich, Mass.; George E. Selecman, Salem; Randall Sword, Danvers, both of Mass.

[73] Assignee: Ethicon, Inc., Cincinnati, Ohio

[21] Appl. No.: 779,040

[22] Filed: Oct. 18, 1991

[51] Int. Cl.$^5$ ............................................. A61M 29/00
[52] U.S. Cl. ...................................... 604/164; 604/158
[58] Field of Search ............... 604/157, 158, 164, 165, 604/167

[56] References Cited

U.S. PATENT DOCUMENTS

| | | | |
|---|---|---|---|
| 3,585,996 | 6/1971 | Reynolds et al. | 604/158 |
| 4,535,773 | 8/1985 | Yoon | 604/51 |
| 4,629,450 | 12/1986 | Suzuki et al. | 604/164 |
| 4,670,008 | 6/1987 | Smithe | 604/165 |
| 4,772,264 | 9/1988 | Cragg | 604/165 |
| 4,810,244 | 3/1989 | Allen | 604/164 |
| 4,869,717 | 9/1989 | Adair | 604/164 |
| 4,911,691 | 3/1990 | Greenley | 604/158 |
| 4,966,587 | 10/1990 | Baumgart | 604/164 |
| 4,973,313 | 11/1990 | Katsaros et al. | 604/165 |
| 4,978,334 | 12/1990 | Toye et al. | 604/164 |
| 4,994,027 | 2/1991 | Farrell | 604/164 |
| 5,009,643 | 4/1991 | Reich et al. | 604/165 |
| 5,030,206 | 7/1991 | Lander | 604/164 |
| 5,064,416 | 11/1991 | Newgard et al. | 604/167 |
| 5,092,846 | 3/1992 | Nishijima et al. | 604/165 |
| 5,112,308 | 5/1992 | Olsen et al. | 604/164 |

*Primary Examiner*—Paul J. Hirsch
*Attorney, Agent, or Firm*—Dressler, Goldsmith, Shore, Sutker & Milnamow, Ltd.

[57] ABSTRACT

Trocar assembly devices that include trocar tubes of different diameters to accommodate small and large diameter implements for providing communication into an anatomical cavity and a unique method of utilizing such devices. The trocar assembly devices include an outer or larger diameter trocar tube and an inner or smaller diameter trocar tube. A distal end portion of the inner trocar tube is tapered and extends distally beyond a distal end portion of the outer trocar tube. The tapered end portion is provided with threads formed on an outer surface thereof to facilitate insertion of the device through the skin and into an anatomical cavity

17 Claims, 4 Drawing Sheets

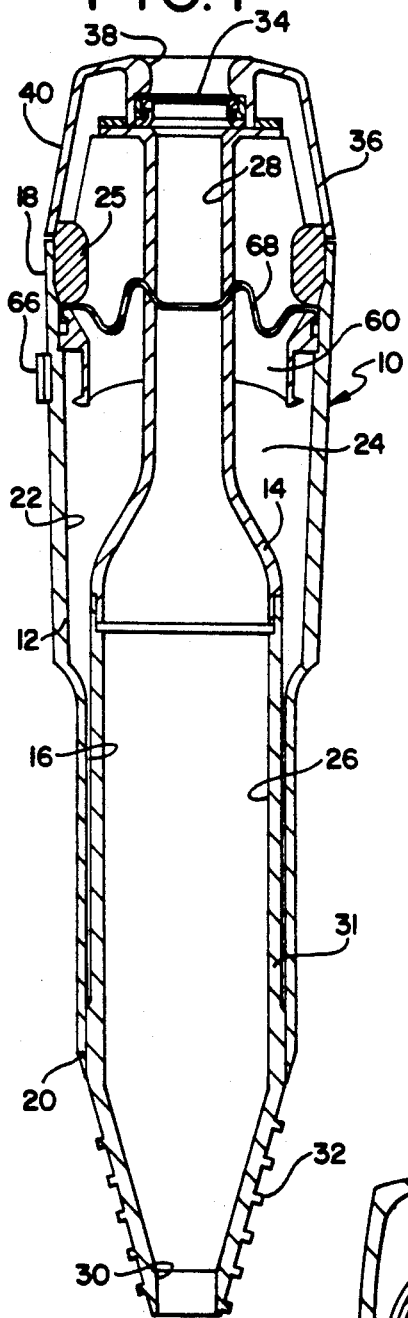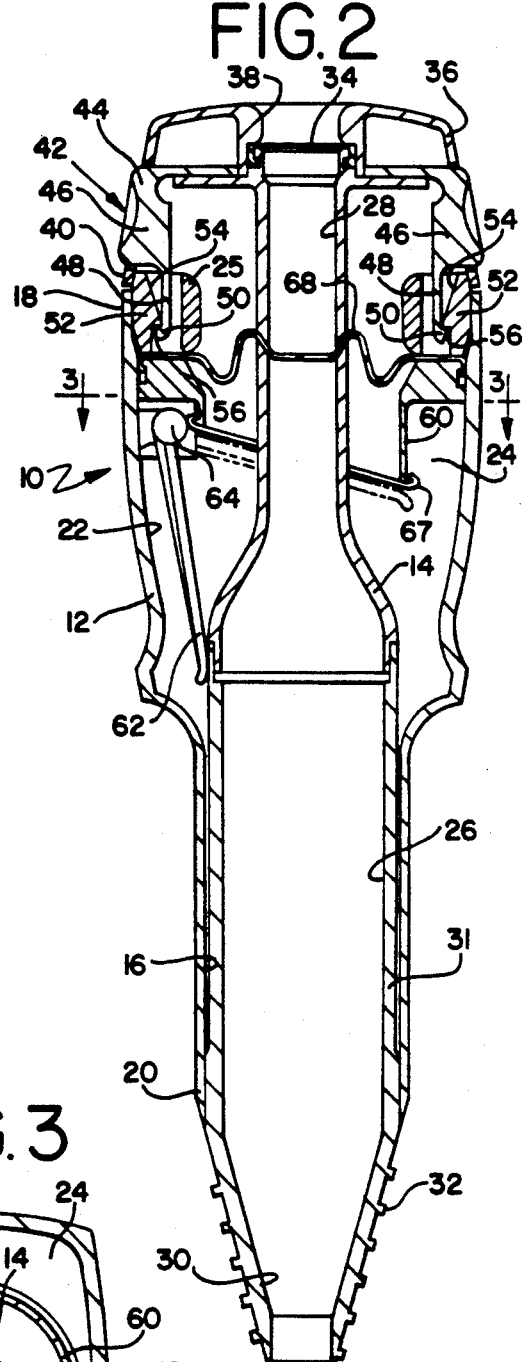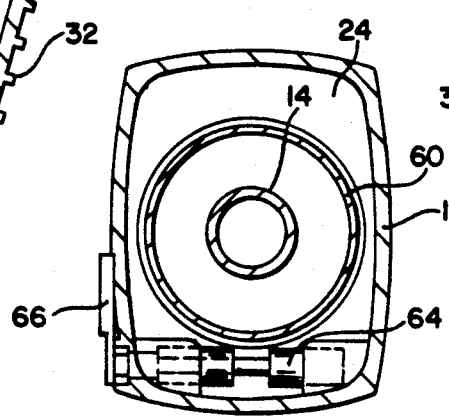

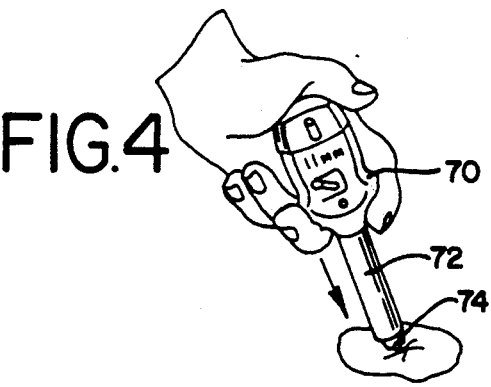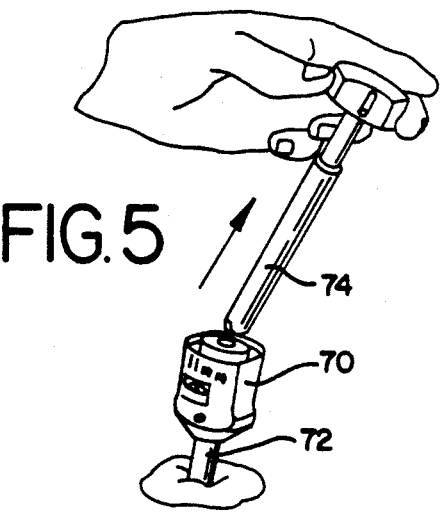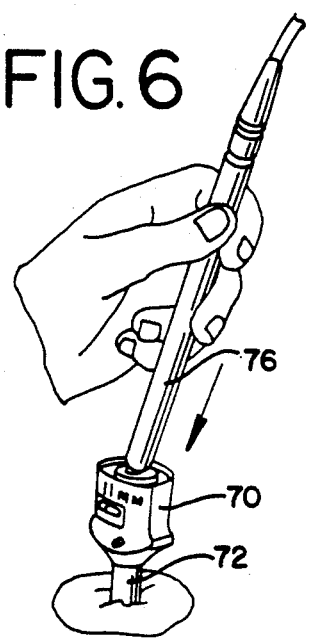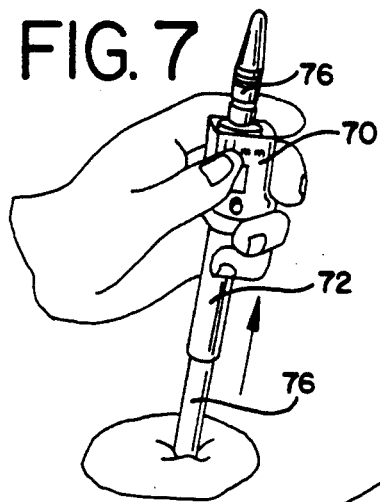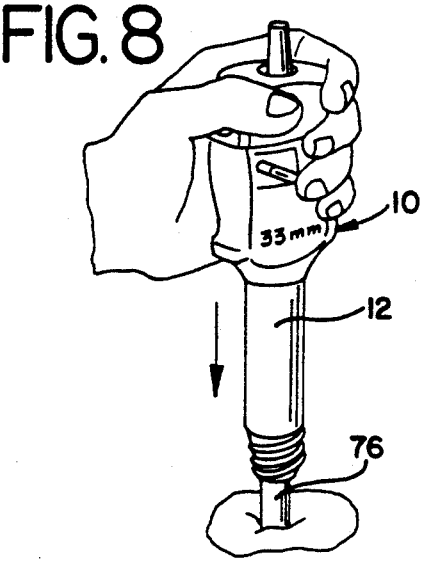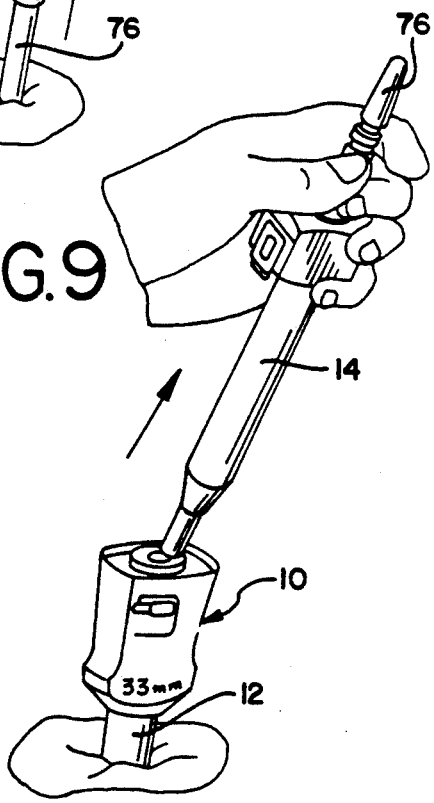

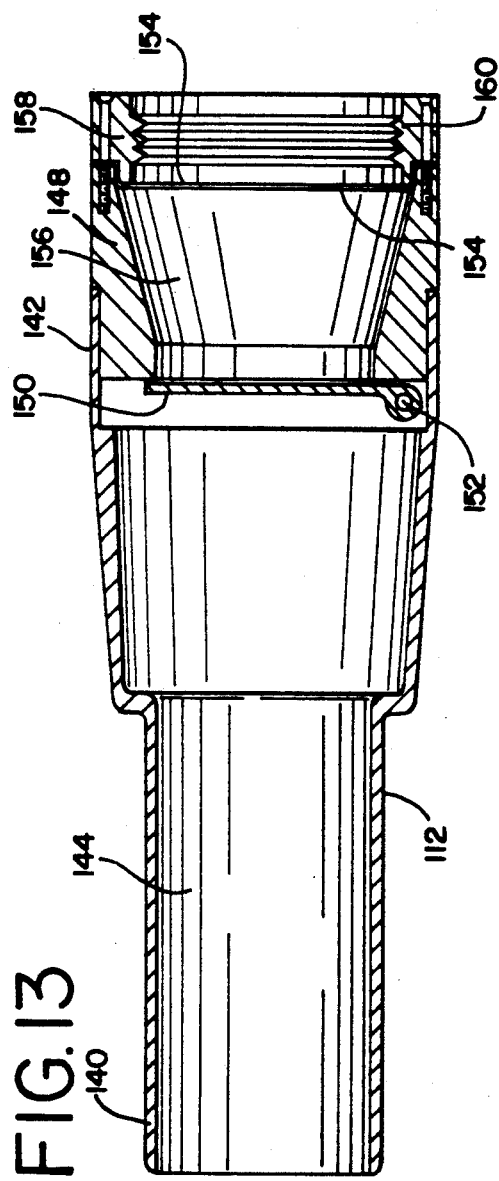
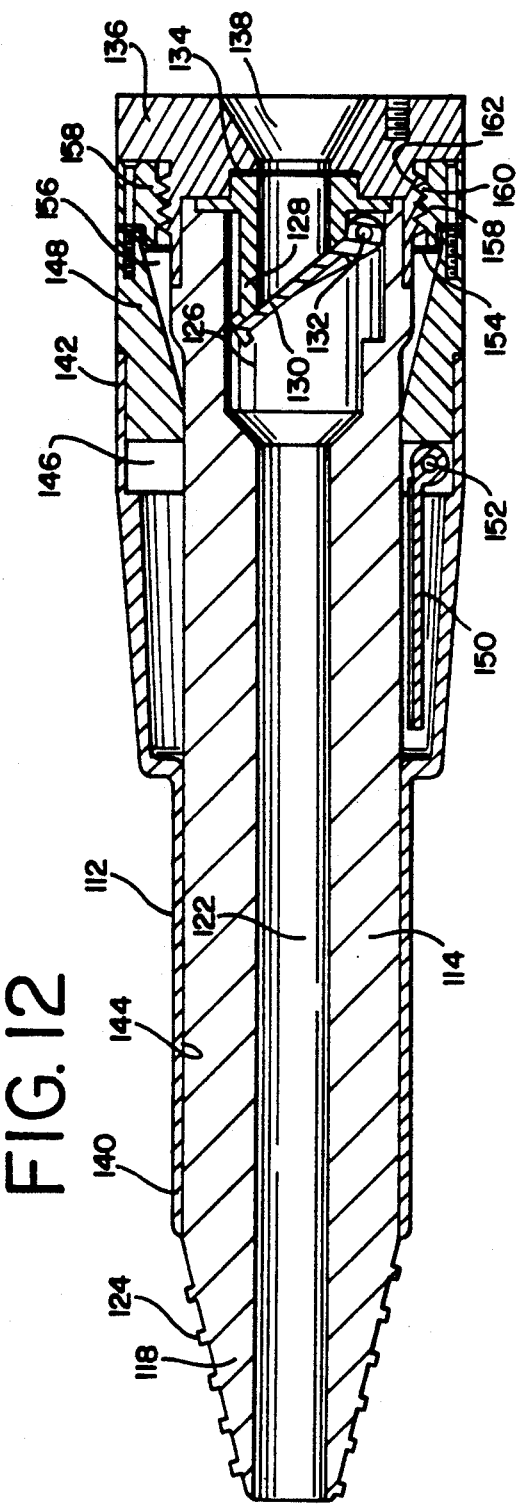

TROCAR METHOD AND APPARATUS

FIELD OF THE INVENTION

This invention generally relates to surgical instruments. More particularly, the invention relates to trocar assembly devices including trocar tubes of different diameters to accommodate small and large diameter tools and implements for providing communication into an anatomical cavity and a unique method of utilizing such devices.

BACKGROUND OF THE INVENTION

A trocar assembly is a surgical instrument that is used to puncture a body cavity. A trocar assembly generally comprises two major components, a trocar tube and an obturator. The trocar tube is inserted through the skin to access a body cavity through the tube in which laparoscopic or arthroscopic surgery and endoscopic procedures are to be performed. In order to penetrate the skin, the distal end of the trocar tube is placed against the skin and an obturator is inserted through the tube. The obturator has a sharp point or cutting edge at its distal end. By applying pressure against the proximal end of the obturator, the sharp point is forced through the skin until it enters the body cavity. The trocar tube is inserted through the perforation made by the obturator and the obturator is withdrawn, leaving the trocar tube as an access-way to the body cavity. Examples of trocar assemblies are disclosed in U.S. Pat. No. 4,535,773.

Trocar assemblies currently range in size up to about 12 mm in diameter. As new medical procedures and tools and implements emerge, trocar assemblies having larger diameter interior lumens will be required. It is frequently necessary to utilize different size tools and implements during a medical procedure. It has heretofore been necessary to utilize multiple trocar assemblies during a medical procedure to accommodate implements and tools of different diameters.

There is a need for trocar assembly devices and methods of utilizing such devices that are compatible with the expanding number of large size implements and tools that may be required during a medical procedure. Such devices would reduce the number of trocar assemblies presently required during many medical procedures.

SUMMARY OF THE INVENTION

In accordance with a preferred embodiment of the invention, a trocar assembly is provided that includes an outer or larger diameter trocar tube and an inner or smaller diameter trocar tube. The inner trocar tube is removably received through the interior lumen defined by the outer trocar tube. The inner and outer trocar tubes have open distal and proximal end portions. The inner trocar tube defines an interior lumen that has a diameter that is less than the diameter of the interior lumen defined by the outer trocar tube.

The distal end portion of the inner trocar tube is tapered and extends distally beyond the distal end portion of the outer trocar tube. The tapered distal end portion is provided with threads formed on an outer surface thereof to facilitate insertion thereof through the skin and into an anatomical cavity.

The proximal end portion of the inner trocar tube includes a sealing means for sealing against smaller diameter implements that are extended therethrough.

The proximal end portion of the outer trocar tube includes a sealing means for sealing against an outer surface of the inner trocar tube when extended therethrough or against larger diameter implements that may be extended therethrough upon removal of the inner trocar tube therefrom. A valve means is preferably provided at the proximal end portion of the outer trocar tube to automatically close off the interior lumen thereof when the inner trocar tube or any implements are removed therefrom.

In accordance with the invention a unique method is provided for positioning a large diameter trocar tube through the skin and into an anatomical cavity. The method is particularly applicable for use in conjunction with the unique trocar device of the present invention. A first conventional trocar assembly having a small diameter trocar tube is directed through the skin and into the anatomical cavity. An elongated dilator member is directed through the trocar tube of the first trocar assembly into the anatomical cavity and the first trocar assembly is removed while maintaining the dilator member in the anatomical cavity.

A second trocar assembly, of the type constructed in accordance with this invention, having a large diameter outer trocar tube, is directed around the dilator member through the skin and into the anatomical cavity. The dilator member is removed from the second trocar assembly while maintaining the large diameter outer trocar tube in the anatomical cavity. The second trocar assembly preferably includes an inner trocar tube of a reduced diameter for receiving the dilator member therethrough. The distal end of the inner trocar tube extends beyond the distal end of the outer trocar tube and is provided with a threaded surface that is tapered to facilitate the directing of the outer trocar tube through the skin and into the anatomical cavity.

In accordance with an alternative embodiment of the present invention, a trocar assembly is provided that includes an outer trocar tube and an inner trocar tube. The inner trocar tube is extendable through the outer trocar tube and has an interior lumen that has a diameter which is less than the diameter of the interior lumen defined by the outer trocar tube. An obturator means is extendable through the inner trocar tube and has a distal end portion that extends through the distal end portion of the inner trocar tube.

The distal end portion of the inner trocar tube is tapered and extends beyond the distal end portion of the outer trocar tube. The tapered distal end portion of the inner trocar tube may be provided with threads to facilitate insertion of the trocar assembly.

The proximal end portion of the outer trocar tube is provided with a valve member that is movable between a first position sealing an open proximal end thereof and a second position permitting the inner trocar tube or an implement to extend therethrough. The proximal end portion of the inner trocar tube preferably includes a valve member movable between a first position sealing an open proximal end thereof and a second position permitting an obturator means or an implement to extend therethrough.

BRIEF DESCRIPTION OF THE DRAWING

A more complete appreciation of this invention, and many of the attendant advantages thereof, will be readily apparent as the same becomes better understood by reference to the following detailed description when considered in conjunction with the accompanying drawings in which like reference numerals indicate the same or similar components, wherein:

FIG. 1 is a cross-sectional view taken through a trocar assembly constructed in accordance with a preferred embodiment of the invention;

FIG. 2 is a cross-sectional view of the trocar assembly shown in FIG. 1 through a plane that is oriented 90° from the plane through which the cross-section of FIG. 1 is taken;

FIG. 3 is a cross-sectional view taken along line 3—3 in FIG. 2;

FIGS. 4–9 illustrate the steps of a method of positioning a large diameter trocar tube through the skin and into an anatomical cavity in accordance with the invention;

FIG. 12 is a cross-sectional view of the trocar assembly shown in FIG. 11 with the obturator removed; and FIG. 13 is a cross-sectional view of the trocar assembly shown in FIG. 12 with the inner trocar tube removed.

DETAILED DESCRIPTION OF PREFERRED EMBODIMENTS

Figure 10:
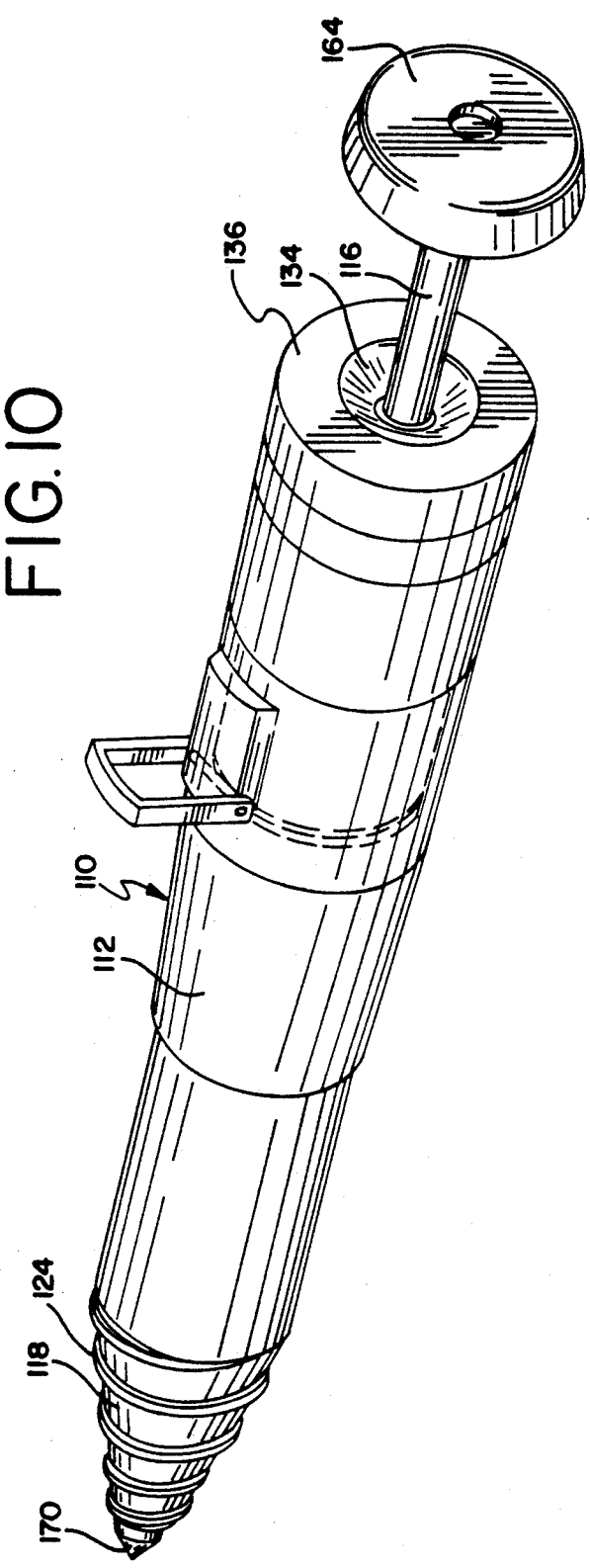
FIG. 10 is a perspective view of an alternative embodiment of a trocar assembly in accordance with the invention, with the obturator partially extended into the trocar tube.

Referring to FIGS. 1–3, a trocar assembly 10 constructed in accordance with the present invention includes an outer trocar tube 12 and an inner trocar tube 14. Inner trocar tube 14 is extendable through outer trocar tube 12.

Outer trocar tube 12 defines an interior lumen 16 and has an open proximal end portion 18 and an open distal end portion 20. The diameter of trocar tube 12 at its distal end of distal end portion 20 is preferably in the range from about 15.0 mm to about 50.0 mm, and most preferably in the range from about 30.0 mm to about 40.0 mm. The proximal end portion 18 of outer trocar tube 12 is of increased dimensions to form a handle or housing portion 22 defining a chamber 24. The opening in the proximal end of the housing is formed by ring 25.

Inner trocar tube 14 defines an interior lumen 26 and has an open proximal end portion 28 and an open distal end portion 30. The diameter of trocar tube 14 at the distal end of its distal end portion 30 is preferably in the range from about 5.0 mm to about 15.0 mm, and most preferably in the range from about 10.0 mm to about 12.0 mm. For reasons that will hereinbelow become more apparent, trocar tube 14 has an intermediate portion 31 that has an increased diameter such that the outer surface thereof slidingly contacts the inner surface of outer trocar tube 12. The diameter of the proximal end portion 28 of trocar tube 14 is substantially equal to the diameter of distal end portion 30. The distal end portion 30 extends distally beyond the distal end of trocar tube 12 and tapers inwardly as it extends towards the distal end thereof. The outer surface of distal end portion 30 preferably has square toothed helical threads 32 formed thereon.

The proximal end portion 28 of inner trocar tube 14 is provided with an annular or apertured sealing gasket 34 to seal against an implement directed therethrough, as is well known in the art. A cap member 36 is attached to the proximal end portion 28 and has an opening 38 in axial alignment with sealing gasket 34. Cap member 36 has side walls 40 that extend towards the proximal edge of housing portion 22.

As best seen in FIG. 2, a latch assembly 42 is provided to releasably attach cap member 36 and inner trocar tube 14 attached thereto to housing portion 22 of outer trocar tube 12 via ring 25 attached to housing portion 22. Latch assembly 42 includes a latch member 44 having a pair of flexible latch activator portions 46 that extend outwardly from openings through opposite sides of cap member 36 and a latch finger portion 48 defining a retaining flange portion 50 associated with each activator portion 46. Ring 25 of the outer trocar assembly is formed with a pair of retaining portions 52 each of which defines a ramp section 54 and a recessed or lip section 56. As inner trocar tube 14 is extended into outer trocar 12 the finger portions 48 of latch member 44 contact a corresponding ramp section 54 and are deflected inwardly as they ride down ramp section 54. When the flange portions 50 reach the lip sections 56 they snap outwardly into locking engagement therewith, as shown in FIG. 2. When it is necessary to remove trocar tube 14 from trocar tube 12, the activator portions 46 are depressed inwardly causing the flange portions 50 to move inwardly beyond the inner projections of lip sections 56, thus permitting trocar tube 14 to be removed from trocar tube 12.

A generally tubular valve seat member 60 is located in chamber 24 at the proximal end portion 18 of outer trocar tube 12. Valve seat member 60 is preferably angled, as best seen in FIG. 2. A flap valve member 62 of known construction is suitably hinged at 64 and is movable between a sealing position in sealing engagement with valve seat member 60, as shown in phantom lines in FIG. 2, and an open position removed from valve seat member 60, as shown in solid lines in FIG. 2. Valve member 62 is biased into its sealing position by a suitable spring means (not shown). A lever member 66 located outside of chamber 24 is attached to hinge 64 to permit manual movement of valve member 62 between its sealing position against a sealing gasket 67 attached to seat 60 into its open position against the spring bias. A sealing gasket 68 is provided at the proximal end of valve seat member 60 to seal against the outer surface of trocar tube 14 or an implement as it extends therethrough. Sealing gasket 68 is preferably a bellows seal to facilitate maintaining a seal during radial motion of instruments inserted therethrough.

The operation and unique features of device 10 will become more apparent from the following description of a unique method of positioning a large diameter trocar tube into an anatomical cavity. While the method of the present invention will be described in cooperation with device 10, it is anticipated that other trocar devices may be utilized to practice the unique method.

Referring to FIG. 4, a conventional trocar device 70 having a small diameter trocar tube 72 in the range from about 10.0 mm to about 12.0 mm, most preferably about 11 mm, is directed through the skin into an anatomical cavity by utilizing an obturator 74 in a well known manner. As depicted in FIG. 5, the obturator 74 associated with trocar device 70 is removed from the trocar tube 72 leaving trocar tube 72 extending into the anatomical cavity. An elongated tubular or dilator member 76 having blunt end portions is directed through trocar tube 72 into the anatomical cavity as shown in FIG. 6.

Referring to FIG. 7, trocar tube 70 is removed and the dilator member 76 is maintained in the anatomical cavity to maintain the opening into the anatomical cavity. A trocar assembly 10, of the type discussed hereinabove and shown in FIGS. 1-3, is directed around the dilator member 76 through the skin and into the anatomical cavity as depicted in FIG. 8. The dilator member 76 extends through the inner trocar tube 14 that is positioned in outer trocar tube 12. As the distal end of the threaded distal end portion 30 contacts the skin, trocar assembly 10 is rotated to facilitate its passage through the skin and adjacent tissue into the anatomical cavity. Referring to FIG. 9, after the trocar assembly 10 is positioned in place in the anatomical cavity, the dilator member 76 and the inner trocar tube 14 are removed from the trocar assembly 10 by releasing latch assembly 42, while maintaining the outer trocar tube 12 positioned in the anatomical cavity. As tube 14 is removed from tube 12 valve member 62 moves into its sealing position.

Referring to FIGS. 10-13, a trocar assembly 110 constructed in accordance with an alternative embodiment of the present invention includes an outer trocar tube 112, an inner trocar tube 114, and an obturator 116. Inner trocar tube 114 is extendable through outer trocar tube 112 and obturator 116 is extendable through inner trocar tube 114.

Figure 11:
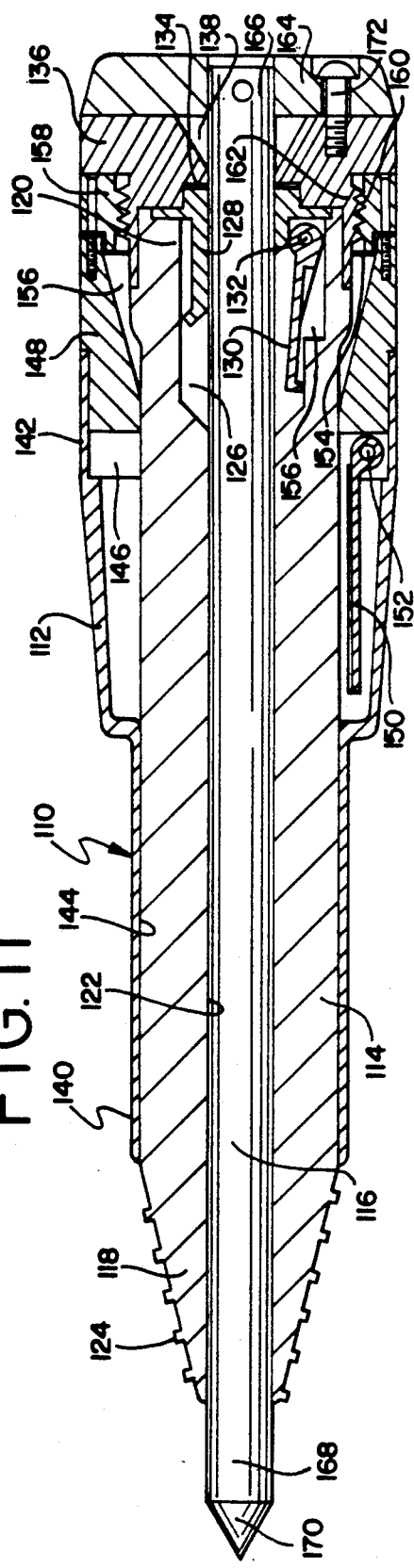
FIG. 11 is a cross-sectional view of the trocar assembly shown in FIG. 10 in an assembled condition.

As best seen in FIGS. 11 and 12, inner trocar tube 114 has an open distal end portion 118 and an open proximal end portion 120 that define an interior lumen 122 extending therebetween. The diameter of lumen 122 is preferably in the range from about 5.0 mm to about 15.0 mm, and most preferably in the range from about 10.0 mm to about 12.0 mm. The distal end portion 118 of trocar tube 114 is preferably tapered and may be provided with male threads 124 formed on a outer surface thereof to facilitate the passage thereof through an aperture formed in the tissue. The proximal end portion 120 has a chamber 126 of increased diameter formed therein that receives a generally tubular valve seat member 128 at its proximal end. Valve seat member 128 is preferably angled at its distal end. A flap valve member 130 of known construction is suitably hinged at 132 and is movable between a sealing position in sealing contact with valve seat member 128, as seen in FIG. 12, and an open position removed from valve seat member 128, as seen in FIG. 11. Valve member 130 is biased into its sealing position by a spring member (not shown) in a well known manner. At the proximal end of valve seat member 128 an apertured sealing gasket 134 is provided to seal against the outer surface of obturator 116 or an implement as it extends therethrough. Gasket 134 is preferably mounted in an manner that permits replacement thereof with gaskets of different diameter apertures to permit the trocar tube to be used with instruments of many different sizes. Valve seat member 128 and sealing gasket 134 are held in place by a cap member 136 releasably secured to the proximal end portion 120 of inner trocar tube 114. Cap member 136 is provided with a passageway 138 that is preferably tapered outwardly to facilitate the insertion of an obturator or an instrument thereinto.

Referring to FIG. 13, outer trocar tube 112 has an open distal end portion 140 and an open proximal end portion 142 that define an interior lumen 144 extending therebetween. The diameter of lumen 144 is preferably in the range from about 15.0 mm to about 50.0 mm and most preferably in the range from about 30.0 mm to about 40.0 mm. The distal end portion 140 preferably has an inner diameter that is slightly greater than the outer diameter of an intermediate portion of inner trocar tube 114. The proximal end portion 142 of trocar tube 112 defines a chamber 146 of increased diameter that receives a generally cylindrical valve seat member 148. A flap valve member 150 of known construction is suitably hinged at 152 and is movable between a sealing position in sealing contact with valve seat member 148, as seen in FIG. 13, and an open position removed from valve seat member 148, as seen in FIG. 11. Valve member 150 is biased into its sealing position by a spring member (not shown) in a well known manner.

At the proximal end of valve seat member 148 an apertured sealing gasket 154 is provided to seal against the outer surface of inner trocar tube 114 or an implement as it extends therethrough. Gasket 154 is preferably mounted in a manner that permits replacement thereof with gaskets of different diameter apertures to permit the outer trocar tube to be used with instruments of many different sizes. A passageway 156 is provided through valve seat member 148 that is preferably tapered outwardly to facilitate the insertion of the inner trocar tube 114 or an implement thereinto. Sealing gasket 154 is held in place by a cap member 158 releasably secured to the proximal end portion of valve seat member 148. As best seen in FIG. 13, cap member 158 is provided with internal threads 160 to receive cooperating external threads 162 formed on cap member 136.

Referring to FIG. 11, obturator 116 is provided with an obturator handle 164 at its proximal end 166 and its distal end 168 is sharpened to a point 170 or may be formed with one or more sharpened cutting blades. Distal end 168 extends beyond the distal end 118 of inner trocar tube 14 when the obturator 6 is extended within lumen 122. A fastener 172 or other suitable fastening means may be provided to releasably secure handle 164 to cap member 136

The unique features of trocar assembly 110 will become more apparent from the following description of the operation thereof. Trocar assembly 110, as shown in FIG. 11, is inserted through the skin to access an anatomical cavity. The distal end 168 of obturator 116 is placed against the skin and pressure is applied against the obturator handle 164 to cause the sharp point 170 to pierce the skin and enter the body. As the distal end portion 118 of inner trocar tube 114 contacts the skin, the trocar assembly 110 is rotated causing the threads 124 to facilitate its passage through the skin and into the anatomical cavity.

After the trocar assembly is appropriately positioned, the obturator 116 is removed and the trocar assembly 110 is as shown in FIG. 12. As is known in the art, small diameter implements or tools may be directed through passageway 138, sealing gasket 134 and lumen 122 into the body. As the implement is directed through member 128, the valve member 130 is urged into its open position.

When it is necessary to direct implements or tools having a diameter greater than the diameter of lumen 122, inner trocar tube 114 is removed from outer trocar tube 112 leaving behind the large diameter outer trocar tube 112, as shown in FIG. 13. The larger diameter implements and tools may be directed through passageway 156, sealing gasket 154 and lumen 144 into the body. As the implement is directed through member chamber 146, the valve member 150 is urged into its open position.

From the foregoing, it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:

1. A method of positioning a large diameter trocar tube in an anatomical cavity, comprising the steps of:
   (a) directing a first trocar assembly having a small diameter trocar tube through the skin and into the anatomical cavity;
   (b) directing an elongated member through the trocar tube of the first trocar assembly and into the anatomical cavity;
   (c) removing the first trocar assembly from the anatomical cavity while maintaining the elongated member in the anatomical cavity;
   (d) directing a second trocar assembly having a large diameter outer trocar tube and a small diameter inner trocar tube around the elongated member through the skin and into the anatomical cavity; and
   (e) removing the elongated member and the inner trocar tube from the anatomical cavity through the outer trocar tube of the second trocar assembly while maintaining the outer trocar tube in the anatomical cavity.

2. The method as defined in claim 1 further including the step of directing an obturator member through the trocar tube of the first trocar assembly to pierce the skin immediately prior to directing the first trocar assembly through the skin.

3. The method as defined in claim 2 further including the step of removing the obturator member from the first trocar assembly prior to directing the elongated member through the first trocar assembly.

4. The method as defined in claim 1 further including the step of providing an inner trocar tube having a reduced diameter within the outer trocar tube of the second trocar assembly for receiving the elongated member therethrough.

5. The method as defined in claim 4 wherein a distal end portion of the inner trocar tube extends distally beyond a distal end portion of the outer trocar tube of the second trocar assembly, said distal end portion of said inner trocar tube includes a tapered portion provided with threads to facilitate the directing of the outer trocar tube of the second trocar assembly through the skin.

6. The method as defined in claim 5 further including the step of rotating the inner trocar tube while it is being directed through the skin.

7. A trocar assembly for providing communication into an anatomical cavity, comprising:
   (a) an outer trocar tube defining an interior lumen, said outer trocar tube having an open proximal end portion and an open distal end portion;
   (b) an inner trocar tube defining an interior lumen, said inner trocar tube having an open proximal end portion and an open distal end portion, said proximal end portion of said inner trocar tube having an annular seal means positioned therein for sealing against implements that extend through said inner trocar tube, said inner trocar tube being removably received within the interior lumen of said outer trocar tube, said interior lumen of said inner trocar tube having a diameter that is less than the diameter of said interior lumen of said outer trocar tube, said distal end portion of said inner trocar tube extending distally beyond the distal end portion of said outer trocar tube, said distal end portion of said inner trocar tube being tapered distally and inwardly and including threads formed on an outer surface thereof; and
   (c) said proximal end portion of said outer trocar tube including a valve means having a valve member movable between a first position sealing said open proximal end portion of said outer trocar tube and a second position permitting said inner trocar tube or an implement to extend through said outer trocar tube.

8. The trocar assembly as defined in claim 7 wherein said distal end portion of said inner trocar tube extends distally beyond the distal end portion of said outer trocar tube.

9. The trocar assembly as defined in claim 8 wherein said distal end portion of said inner trocar tube is tapered and has threads formed on an outer surface thereof.

10. The trocar assembly as defined in claim 7 wherein the diameter of the openings at the distal end portion and the proximal end portion of said inner trocar tube are less than the diameter of a portion of said inner trocar tube that extends intermediate said distal end portion and said proximal end portion.

11. The trocar assembly as defined in claim 7 wherein an annular seal means is positioned at the proximal end portion of said outer tube for sealing against said inner trocar tube or an implement that extends through said outer trocar tube.

12. The trocar assembly as defined in claim 7 wherein the proximal end portion of said outer and inner trocar tubes are provided with cooperating latch means for releasably attaching the tubes together.

13. A trocar assembly for providing communication into an anatomical cavity, comprising:
   (a) an outer trocar tube defining an interior lumen, said outer trocar tube having an open proximal end portion and an open distal end portion;
   (b) an inner trocar tube defining an interior lumen, said inner trocar tube having an open proximal end portion and an open distal end portion, said proximal end portion of said inner trocar tube having an annular seal means positioned therein for sealing against implements that extend through said inner trocar tube, said inner trocar tube being extendable through the interior lumen of said outer trocar tube, said interior lumen of said inner trocar tube having a diameter that is less than the diameter of said interior lumen of said outer trocar tube;
   (c) an obturator means having a proximate end portion and a distal end portion, said obturator means being extendable through said interior lumen of said inner trocar tube; and
   (d) said proximal end portion of said outer trocar tube including a valve means having a valve member movable between a first position sealing said open proximal end portion of said outer trocar tube and a second position permitting said inner trocar tube or an implement to extend through said outer trocar tube.

14. The trocar assembly as defined in claim 13 wherein said distal end portion of said obturator means is extendable through said distal end portion of said inner trocar tube.

15. The trocar assembly as defined in claim 14 wherein said distal end portion of said obturator means includes a conical tip.

16. The trocar assembly as defined in claim 15 wherein said distal end portion of said inner trocar tube is tapered toward said conical tip and extends beyond said distal end portion of said outer trocar tube.

17. The trocar assembly as defined in claim 16 wherein said distal end portion of said inner trocar tube has threads formed on a outer surface thereof.

* * * * *